(12) United States Patent
Elodie

(10) Patent No.: US 9,084,899 B2
(45) Date of Patent: *Jul. 21, 2015

(54) ACTIVE IMPLANTABLE MEDICAL DEVICE HAVING ANTITACHYCARDIA ATRIAL AND ANTIBRADYCARDIA VENTRICULAR PACING

(71) Applicant: SORIN CRM S.A.S., Clarmart Cedex (FR)

(72) Inventor: Vincent Elodie, Antony (FR)

(73) Assignee: SORIN CRM S.A.S., Clamart Cedex (FR)

( * ) Notice: Subject to any disclaimer, the term of this patent is extended or adjusted under 35 U.S.C. 154(b) by 5 days.

This patent is subject to a terminal disclaimer.

(21) Appl. No.: 14/047,461

(22) Filed: Oct. 7, 2013

(65) Prior Publication Data
US 2014/0039569 A1 Feb. 6, 2014

Related U.S. Application Data

(63) Continuation of application No. 12/636,677, filed on Dec. 11, 2009, now Pat. No. 8,554,319.

(30) Foreign Application Priority Data

Dec. 12, 2008 (FR) ...................... 08 06968

(51) Int. Cl.
*A61N 1/365* (2006.01)
*A61N 1/362* (2006.01)
*A61N 1/39* (2006.01)

(52) U.S. Cl.
CPC ............ *A61N 1/3624* (2013.01); *A61N 1/3622* (2013.01); *A61N 1/36578* (2013.01); *A61N 1/3987* (2013.01); *A61N 1/36585* (2013.01)

(58) Field of Classification Search
None
See application file for complete search history.

(56) References Cited

U.S. PATENT DOCUMENTS

| 4,719,921 A | 1/1988 | Chirife |
| 5,549,652 A | 8/1996 | McClure et al. |
| 2004/0147968 A1* | 7/2004 | Casset ............................ 607/17 |

FOREIGN PATENT DOCUMENTS

| EP | 0 515 319 | 11/1992 |
| EP | 0 655 260 | 5/1995 |

(Continued)

OTHER PUBLICATIONS

Search Report for French Application No. FR 0806968 FA 715751, mail date Sep. 23, 2009, 2 pages.

*Primary Examiner* — Brian T Gedeon
(74) *Attorney, Agent, or Firm* — Foley & Lardner LLP

(57) ABSTRACT

An implantable medical device includes a mechanical activity sensor configured to sense movements produced by contractions of a ventricular cavity and output a mechanical activity signal representative of the contractions. The implantable medical device also includes one or more circuits configured to detect a plurality of spontaneous ventricular depolarizations based on electrical potentials representative of the spontaneous ventricular depolarizations, calculate an escape interval, and provide an antibradycardia ventricular pacing therapy in an absence of a detected spontaneous ventricular event after the escape interval. The circuits calculate the escape interval by calculating a first escape interval based on successive detected spontaneous ventricular depolarizations and a second escape interval based on the mechanical activity signal from the mechanical activity sensor, and selecting one of the first escape interval and the second escape interval, wherein the second escape interval is selected in response to a delivery of an antitachycardia atrial pacing therapy.

20 Claims, 3 Drawing Sheets

(56) References Cited

FOREIGN PATENT DOCUMENTS

| WO | WO-95/03086 | 2/1995 |
| WO | WO-95/13741 | 5/1995 |
| WO | WO-95/27531 | 10/1995 |
| WO | WO-2008/054261 | 5/2008 |

\* cited by examiner

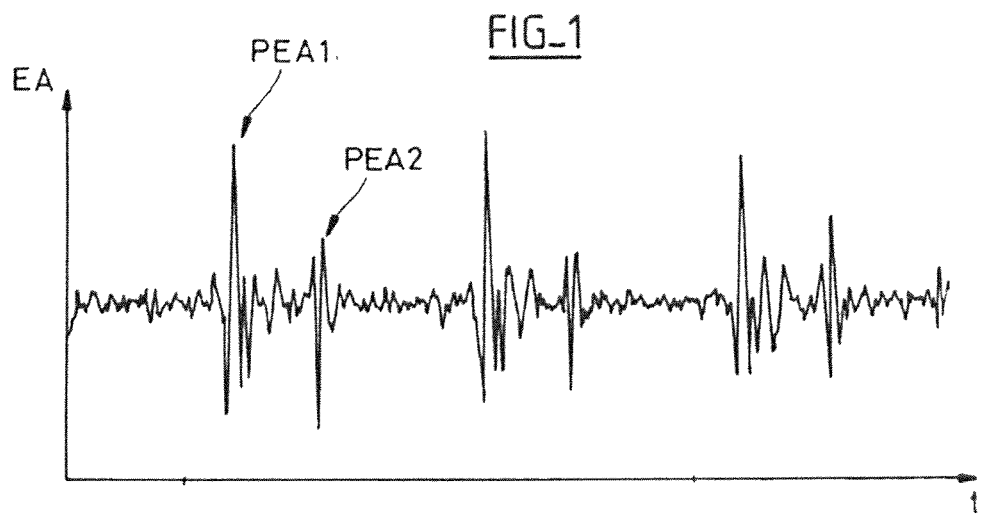
FIG_1
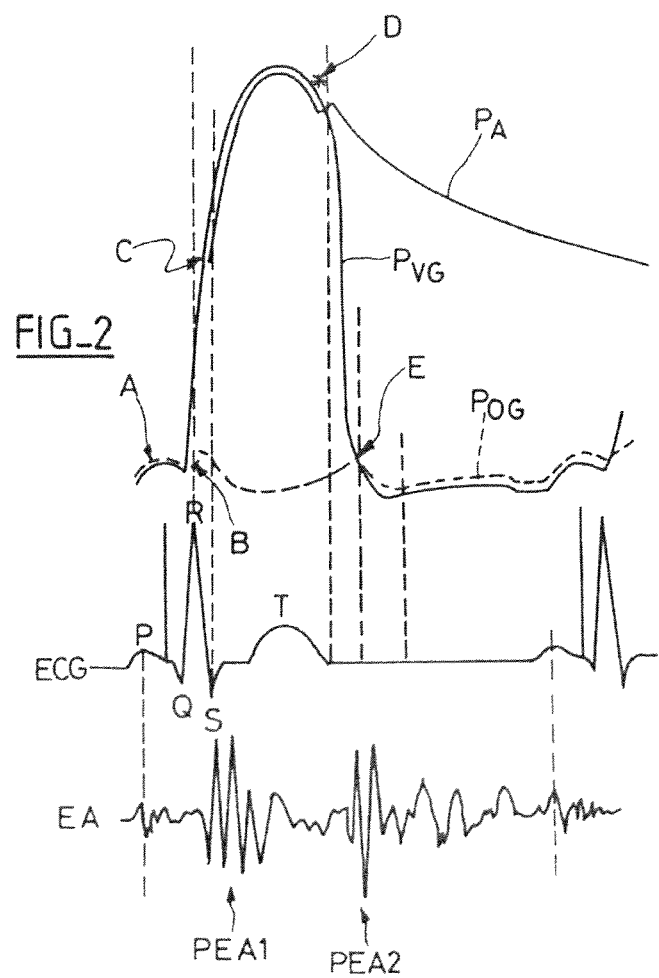
FIG_2

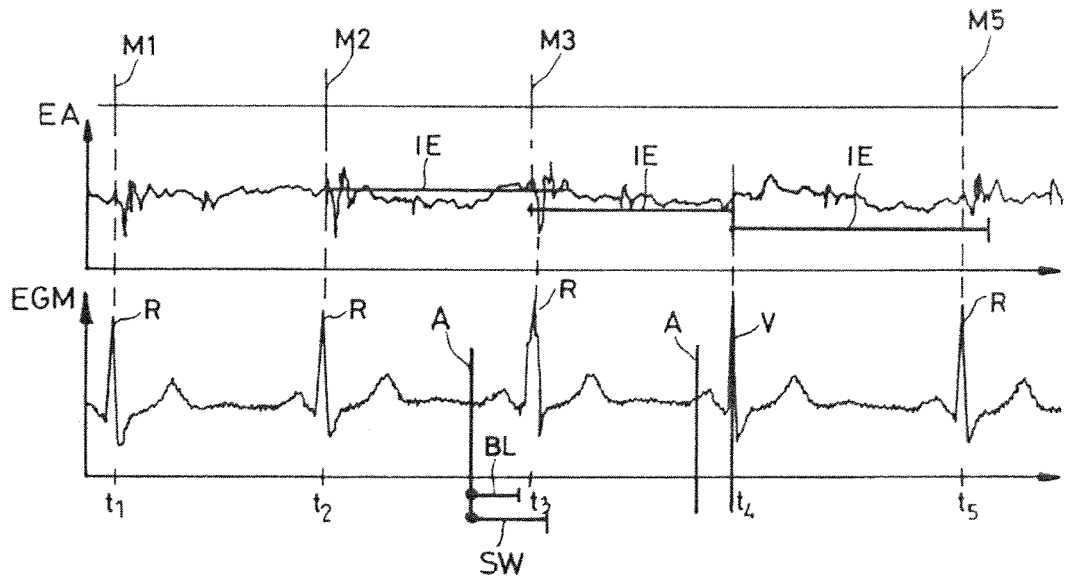
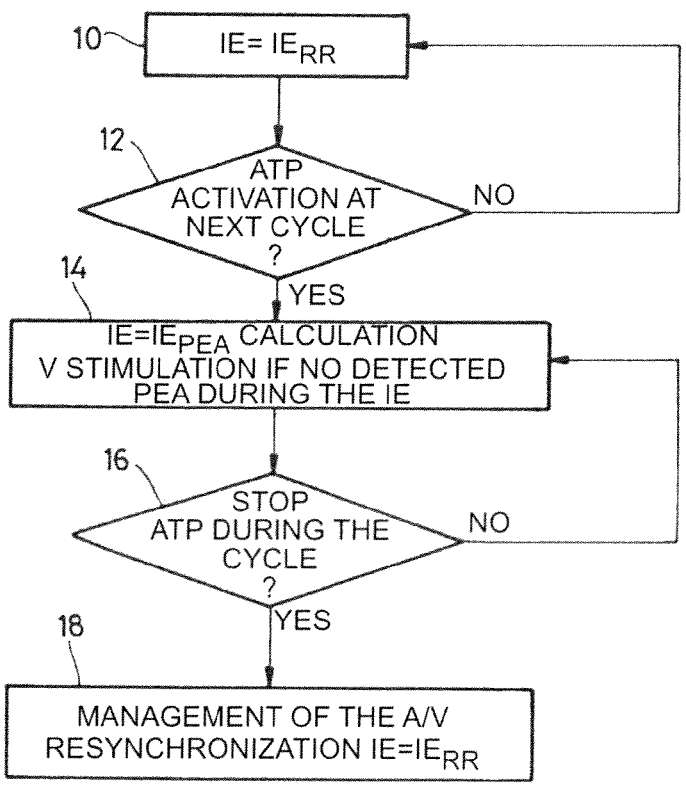

ACTIVE IMPLANTABLE MEDICAL DEVICE HAVING ANTITACHYCARDIA ATRIAL AND ANTIBRADYCARDIA VENTRICULAR PACING

CROSS-REFERENCE TO RELATED PATENT APPLICATIONS

The present application is a continuation of U.S. application No. 12/636,677, filed Dec. 11, 2009, which claims the benefit of and priority to French Patent Application No. 0806968, filed Dec. 12, 2008. U.S. application No. 12/636,677 and French Patent Application No. 0806968 are both incorporated by reference herein in their entireties.

BACKGROUND OF THE INVENTION

The present invention relates to "implantable medical devices" such as those defined by the Jun. 20, 1990 Directive 90/385/EEC of the Council of European Communities, specifically to implantable devices that continuously monitor heart rhythm and deliver to the heart, if necessary, electrical stimulation pulses for cardiac resynchronization and/or defibrillation, in response to an arrhythmia detected by the device. The present invention relates more particularly to those devices that deliver an anti-tachycardia pacing ("ATP") therapy, that is a programmed high-frequency stimulation of the atrium, or a pulse train of stimulations (notably including 30 Hz stimulation. WO95/03086 A1 discloses such an implanted device able to deliver if necessary an ATP stimulation to the patient.

ATP therapy is indicated to treat certain arrhythmias caused by disturbances of the action potentials in the atrium. Therapy by stimulation of the atrium can be applied in case of detection of an abnormal fast heart rhythm of atrial origin (atrial fibrillation or other atrial arrhythmia). It will be called hereinafter "antitachycardia atrial pacing" (also referred to as "ATP-A").

Overall, the decision to apply antitachycardia therapy, and the choice of this therapy (whether an application of a defibrillation shock, or an ATP therapy or a similar type antitachycardia stimulation) is made by an algorithm for detecting and classifying different tachyarrhythmias based on several discrimination criteria. These criteria include, for example, the ventricular rate, the stability of ventricular intervals (namely, RR intervals), the analysis of the atrioventricular association revealed by the stability of the PR interval, and the start-up mode of the tachycardia (presence of an abrupt acceleration and identity of the cavity of origin, ventricular or atrial).

Some of these tachycardias can be treated by activating an antitachycardia atrial pacing (ATP-A).

However, when an antitachycardia pacing in the atrium therapy is delivered, the device is unable to detect ventricular events. This is because the duration of the post atrial pacing ventricular refractory periods, relative to the interval between two consecutive atrial stimulations, effectively blocks any detection of any ventricular depolarization.

Further, ventricular contractions during these arrhythmia episodes can be very irregular or even non-existent, causing the onset of ventricular pauses. It is therefore important to maintain a detection of the ventricular activity during the application of antitachycardia atrial pacing so as, if necessary, to stimulate the ventricle if no spontaneous ventricular event is detected. As will be discussed below, the term "antibradycardia ventricular pacing" refers to this conditional stimulation of the ventricle.

More specifically, disturbances of the atrium and/or ventricle action potentials can cause ventricular arrhythmias. These are generally classified as Supraventricular Tachycardias (SVT) or Ventricular Tachycardias (VT). The SVT is characterized by an abnormal rhythm in the atrium or at the atrioventricular node. The most common SVTs are atrial flutters and atrial fibrillations:

During atrial flutters, the action potentials have a circular atrial path, causing an acceleration of the rate of contraction of the atrium with atrioventricular intermittent conduction (2:1 or 3:1, for example);

As for atrial fibrillation, these are common arrhythmias that correspond to uncontrolled atrial depolarization, leading to a sometimes rapid and often irregular activity of the ventricles thereby reducing the hemodynamics efficiency of the ventricular contraction.

During these atrial arrhythmias, the patient may experience palpitations and complain of malaises, dyspnoea and chest pains. It can be important to treat these arrhythmias in some cases, and the application of antitachycardia pacing is one treatment option.

However, in the presence of a stimulation of the atrium—and thus, especially during the application of an antitachycardia atrial pacing therapy—the electrical detection of the ventricular activity by the device can be masked by the atrial post-stimulation refractory periods.

One solution to this masking problem is to always deliver a ventricular pacing for the duration of the antitachycardia atrial pacing therapy. However, such a ventricular stimulation will always be an asynchronous pacing, because of the refractory periods subsequent to the stimulation and the blanking periods, corresponding to the disconnection of the detection circuits of the amplifier to allow the discharge of the stored energy in the heart at the heart/electrode interface after stimulation. Because of this asynchrony, there is a risk of stimulating a T wave, with the possible consequence of triggering ventricular arrhythmias.

SUMMARY OF THE INVENTION

It is therefore an object of the present invention to overcome these difficulties by proposing a new technique for the detection of ventricular activity during an application of antitachycardia atrial pacing, whereby, if necessary, an antibradycardia pacing stimulation is applied to the ventricle, during the duration of an ATP-A therapy, in a controlled manner (i.e., applied only where needed) and a synchronous manner, so as to minimize any risk of triggering ventricular arrhythmias.

Broadly, the present invention proposes to detect the contraction, or lack of contraction, of the ventricle by detecting a mechanical activity of the ventricle through an acceleration signal produced by a sensor that is responsive to the mechanical activity of the ventricle. In one embodiment, the acceleration signal is an endocardial acceleration signal delivered by an implanted endocardial accelerometer sensor. Such an endocardial acceleration sensor may be present on the ventricular lead, or on another lead, said lead being placed directly into the ventricle (namely, an endocardial lead) or in another position, e.g., in the atrium, to collect the endocardiac acceleration (EA) signal representative of the ventricular contractions. Although the invention will be discussed in the context of an endocardial acceleration sensor, it should be understood that any sensor that allows measuring the mechanical activity of the ventricle may be used, e.g., a pressure responsive sensor, a bio-impedance sensor.

In one particular embodiment, the invention is directed to methods and apparatus for using, during antitachycardia pacing of the atrium, a functional signal (e.g., the EA signal) representative of the mechanical contraction of the ventricle. The mechanical activity signal is used instead of a signal that has originated from the electrical propagation of the depolarization wave. The detection of the ventricular mechanical activity will thus replace the detection of the electrical cardiac activity for the duration of the antitachycardia atrial therapy.

One aspect of the invention is thus directed to an active implantable medical prosthesis that is able to provide cardiac stimulation, resynchronization and/or defibrillation. One suitable device is an improvement of the known type, such as the one disclosed in international publication WO95/03086 A1, having circuits and logic control for atrial and ventricular detection, namely able to detect the occurrence of spontaneous atrial events and spontaneous ventricular events; antitachycardia atrial pacing, able to deliver sequences of low energy atrial pacing pulses at a higher frequency than that of the patient' s sinus rhythm in case of a detected atrial arrhythmia; a calculator that can calculate a ventricular escape interval; and antibradycardia ventricular pacing, able to deliver a conditional ventricular stimulation pulse in the absence of a spontaneous ventricular event detected by the ventricular detection circuits at the end of a ventricular escape interval. In accordance with the present invention, the device also includes a sensor responsive to mechanical activity of the myocardium (herein also called a "mechanical activity sensor"), able to deliver a mechanical activity signal representative of the mechanical movements produced by the contractions of the ventricular cavity; and ventricular detection, able to detect the mechanical activity of the ventricle, including: a primary detection means, able to detect a spontaneous ventricular depolarization electrical potential (R), and an auxiliary detection means, able to recognize and isolate in the mechanical activity signal delivered by the sensor a component associated to a ventricular contraction.

In a manner characteristic of the present invention, the antitachycardia pacing is provided by the circuits that produce atrial pacing, and the auxiliary detection means are implemented in response to an initiation of an antitachycardia atrial pacing stimulation therapy, in order to supplement, and more preferably replace, the primary detection means during the presence of post-atrial pacing refractory periods that might block the detection of a ventricular electrical activity (R) by the primary detection means. In addition, the escape interval calculator includes: means for calculating a first escape interval value ($IE_{RR}$) from the successive moments of occurrence of the spontaneous ventricular depolarization potentials (R) detected by the primary detection means; means for calculating a second escape interval value ($IE_{PEA}$) from the successive moments of occurrence of said ventricular contractions detected by the auxiliary detection means; and means to select the second escape interval value in response to an activation of the antitachycardia atrial stimulating means.

In calculating the second escape interval value, the escape interval calculator preferably limits the escape interval value to a predetermined minimum value, and also averages a plurality of successive escape interval values identified during successive cycles.

The mechanical activity sensor of the myocardium is preferably an acceleration sensor able to deliver an endocardiac acceleration (EA) signal, the auxiliary detection means thus being able to recognize and isolate the endocardiac acceleration signal component that corresponds to a peak of endocardiac acceleration associated with said ventricular contraction. This acceleration sensor may be an endocardial sensor, an epicardial sensor, or a myocardium wall motion sensor.

Alternatively, the mechanical activity sensor may be a pressure sensor or an intracardiac impedance sensor. A combination of one or more of the foregoing sensors (with or without correlation of their signals) may be used.

BRIEF DESCRIPTION OF THE DRAWINGS

Further features, advantages and characteristics of the present invention will now be described in accordance with the following detailed description of a preferred embodiment of the present invention, made with reference to the drawings annexed, in which the same numerical references designate items that are identical or functionally similar from one figure to the next, and in which:

FIG. 1 illustrates an example of an endocardiac acceleration signal EA collected during three successive cardiac cycles;

FIG. 2 is a series of three timing diagrams illustrating various signals characterizing the cardiac activity during a given cycle;

FIG. 3 illustrates endocardiac acceleration and electrogram signals over five successive cardiac cycles representing how the invention manages ventricular pacing on the basis of an endocardiac acceleration signal during the duration of an atrial stimulation; and FIG. 4 is a flow chart illustrating exemplary steps for ventricular pacing management.

DETAILED DESCRIPTION OF THE PREFERRED EMBODIMENTS

Figure 5:
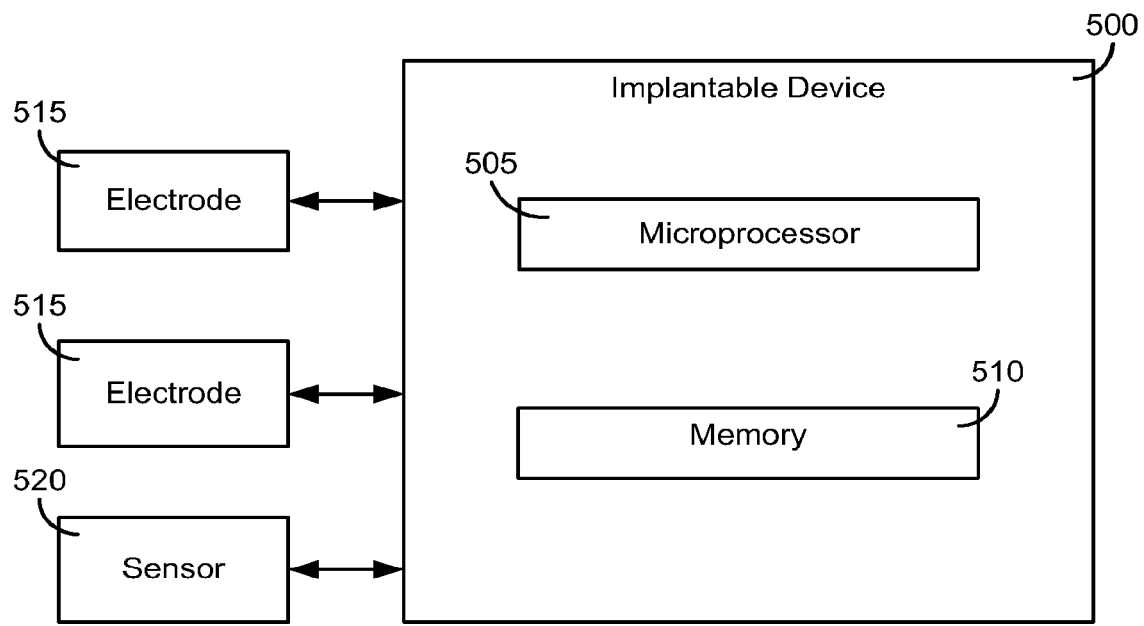
FIG. 5 is a block diagram of an example implantable device.

With reference to the drawings, a preferred embodiment of a device in accordance with the present invention will now be described. As regards to its software aspects, the invention can be implemented by an appropriate programming of the control software of a known pacemaker, for example, of the cardiac pacemaker, resynchronizer and/or defibrillator type, including circuits and control logic or software for the acquisition of mechanical activity signals provided by endocardial leads and/or one or more implanted sensors.

As for hardware, the invention may particularly be applied to implantable devices such as those of the Reply and Paradym families produced and marketed by ELA Medical (also known as Sorin CRM), Montrouge, France. Referring now to FIG. 5, an example implantable device 500, such as these devices, includes programmable microprocessor circuitry 505 to receive, format, and process electrical signals collected by implanted electrodes 515, and to deliver pacing pulses to these electrodes 515. It is possible to transmit by telemetry software that will be stored in a memory 510 of the device 500 and that can be executed by the device 500 to implement the functions of the present invention. The adaptation of these devices to implement the functions of the present invention is believed to be within the abilities of a person of ordinary skill in the art, and therefore will not be described in detail.

It is known how to detect a mechanical activity signal, in particular an endocardiac acceleration signal, using a sensor 520. One suitable technology is disclosed and described, for example, in EP-A-0 515 319 (Sorin Biomedica Cardio SpA) as an endocardial lead that is equipped with a distal stimulation electrode implanted at the ventricle apex, incorporating a microaccelerometer to measure the endocardiac acceleration. The endocardiac acceleration signal thus measured during a cardiac cycle forms, among others, two peaks corresponding to the two major noises that are recognizable in each cycle of a healthy heart. EP-A-0 655 260 (Sorin Biomedica Cardio SpA) describes a way of processing the endocardial acceleration signal delivered by a sensor located in the lead tip to derive, in particular, the temporal position and the amplitude of the two endocardial acceleration peaks. These data are particularly useful for detecting cardiac disorders and triggering or not a defibrillation therapy.

With reference to FIG. 1, variations in three consecutive cardiac cycles of a detected endocardial acceleration (EA) are shown, as measured by a sensor, for example the sensor described in EP-A-0 515 319 cited above, incorporated into an endocardial lead tip placed at the apex of the ventricle. As can be seen, the EA signal forms during a cardiac cycle two main peaks corresponding to the two major noises (sounds S1 and S2 of the phonocardiogram) that are recognizable in each cycle of a healthy heart. Specifically:

The first peak endocardiac acceleration ("PEA1") corresponds to the closure of the mitral and tricuspid valves, at the beginning of the phase of isovolumetric ventricular contraction (systole). Its variations are closely related to variations in pressure in the ventricle (the amplitude of the PEA1 peak being more specifically correlated with the maximum positive change of pressure dP/dt in the left ventricle);

The second peak endocardiac acceleration ("PEA2") corresponds to the phase of isovolumetric ventricular relaxation, and is produced by the sudden deceleration of the moving blood volume in the aorta.

The EA signal also contains at least two other components, of a much lower amplitude, referred to as EA3 and EA4, corresponding to the S3 and S4 sounds of the phonocardiogram.

With reference to FIG. 2, the various signals characterizing the activity of the heart during a cardiac cycle are illustrated, including: a profile of intracardiac pressures at the top third, a record of a surface electrocardiogram (ECG) at the middle third, and the variations in the endocardial acceleration (EA) signal at the lower third.

On the profile of intracardiac pressures, the $P_A$ characteristic shows changes in aortic pressure, the $P_{VG}$ characteristic shows pressure changes in the left ventricle, and the $P_{OG}$ characteristic shows pressure changes in the left atrium. Points A to E correspond to different phases: A, contraction of the atrium, B, closure of the mitral valve, C, opening of the aortic valve, D, closure of the aortic valve, and E, opening of the mitral valve.

The ECG signal includes successively: the P wave corresponding to the depolarization of the atrium, the QRS complex corresponding to the ventricular depolarization and the T wave of ventricular repolarization.

The EA endocardiac acceleration signal is decomposed as follows: the contraction of the atrium (P wave) is followed by the EA1 component, which begins after the QRS complex and is caused by a combination of the closure of atrio-ventricular valves, the opening of the semilunar valves, and the contraction of the left ventricle. The EA2 component that follows is associated with the end of a ventricular systole and is generated by the closure of the semilunar valves.

The temporal position of each peak of endocardiac acceleration, including the peak PEA1 of the EA1 component, can be determined in each cycle by an appropriate processing of the signal delivered by the acceleration sensor.

In FIG. 3, the successive time markers M1, M2, M3, ... Mi delivered by the device are shown on the top line, corresponding to the moments of the beginning of the PEA1 that are detected on the EA signal. The second line gives the EA signal from which these markers are obtained, while the third line is a plot of the EGM signal corresponding to the electrogram.

In general, antibradycardia stimulation of the ventricle involves the calculation by the device of an "escape interval" (IE), which is the time interval counted after a ventricular event (detection of an R spontaneous depolarization or of a V stimulation), after which a stimulation is delivered to the ventricle if no spontaneous event is detected in the same cavity.

The escape interval is usually calculated from the successive moments of occurrence of spontaneous ventricular depolarization potentials (R peaks), on the basis of electrical events detected in the ventricle. This value will then be referred to as "electrical escape interval" and noted $IE_{RR}$. The calculated escape interval is triggered by the detection of a spontaneous or stimulated ventricular event.

In accordance with a preferred embodiment of the present invention, the device also calculates, in conjunction with the escape interval $IE_{RR}$, a second escape interval, referred to as a "mechanical escape interval" and noted $IE_{PEA}$. It is based not on the RR interval but rather on the moments between mechanical contractions of the ventricle, preferably determined from successive determined PEA1 peaks.

Indeed, from the cycle to cycle detection of the PEA, the PEA-PEA interval (i.e., the interval between markers Mi and Mi+1) is determined and monitored. The monitoring of the PEA-PEA interval may be performed:
 continuously,
 only in case of suspicion of a sustained atrial arrhythmia (a situation corresponding to, e.g., a switch of the device operation to a classic fallback mode), or
 only from the last ventricular detection (detection of spontaneous activity having its origin in the ventricle, corresponding to an R peak on the EGM electrogram, see FIG. 2) before the onset of an antitachycardia atrial stimulation.

The mechanical escape interval $IE_{PEA}$ is triggered on each detected spontaneous or paced ventricular event, and calculated using rules similar to the rules used for calculating the electrical escape interval $IE_{RR}$. However, the calculation of the mechanical escape interval in this embodiment is based on successive PEA-PEA intervals instead of successive RR intervals.

FIG. 4 illustrates the different steps of an example of an algorithm from the management of ventricular pacing, according to one embodiment. The initial value of the escape interval (step 10) used by the device is the value of the electrical escape interval IERR triggered upon detection of a spontaneous (R) or stimulated (V) ventricular event. On the last ventricular cycle preceding the application of an antitachycardia atrial therapy (test at step 12), the device starts an escape interval IE.

The electric escape interval $IE_{RR}$ may not be reliably used during an ATP-A therapy because the ventricular refractory periods that follow rapid atrial stimulation may mask the electrical detection of a ventricular spontaneous depolarization. This situation corresponds to the second cardiac cycle illustrated in FIG. 3: the atrial stimulation indicated by the marker triggers both a post-atrial pacing blanking period BL and a safety window SW. During these periods no ventricular sensing is detected by the device. Specifically, in this example, the spontaneous depolarization R at time $t_3$ cannot be detected by the sensing amplifier of ventricular electrical depolarization. However, the ventricular event occurring at time $t_3$ is reliably detected by analyzing the EA signal thanks to the presence of a PEA1 peak, giving a temporal marker M3.

The escape interval IE takes one of the following values (step 14):

the last value of $IE_{RR}$ (or an average value of a last number of (e.g., four) values of $IE_{RR}$), in case the PEA is neither monitored continuously or during atrial arrhythmias, or the last value of $IE_{PEA}$ (or an average value of a last number of (e.g., four) values of $IE_{PEA}$), if the PEA is already monitored before the onset of the atrial therapy, particularly when the PEA is continuously monitored by the device.

At the end of the escape interval IE, if the device has not detected any PEA, a ventricular pacing is delivered, and a new escape interval $IE_{PEA}$ is calculated and started. This situation corresponds to the fourth cycle of the example shown in FIG. 3: whereas for the previous cycles a ventricular contraction was detected (e.g., M1, M2 and M3 markers), in the next cycle no contraction is detected (no M4 marker indicating a contraction of the ventricle). A ventricular pacing (V marker) is then applied by the device to cause a contraction of the ventricle that did not contract spontaneously.

The range of values of the IE escape interval is limited firstly by the maximum frequency stimulation programmed by the physician, and secondly by the base stimulation frequency, and/or the value of maximum ventricular pause, and/or any other appropriate previously defined criterion.

Moreover, some R events produced, e.g., by ventricular extrasystoles (ESV) can lead to a low but detectable amplitude PEA1 signal. To avoid the risk of stimulation in the vulnerable period following such an event, the escape interval IE may be limited to a minimum value, e.g., 1000 ms.

If the antitachycardia atrial pacing ends before the end of the escape interval $IE_{PEA}$ (test at step 16), then (step 18) an atrial stimulation is applied with a delay ($IE_{PEA}$-DAV), if it occurs more than 500 ms after the last atrial pacing, otherwise a ventricular stimulation is applied, so as to allow a satisfactory resynchronization of the atrium and the ventricle.

After the end of the antitachycardia atrial stimulation therapy, the escape interval is preferably recalculated and managed in the usual manner, namely returning to use of the electric escape interval ($IE=IE_{RR}$).

This situation corresponds to the period between times $t_4$ and $t_5$ in the example illustrated in FIG. 3: the device has terminated the atrial stimulation, but the atrium and the ventricle are resynchronized (in the illustrated example, the device detects at the instant $t_5$ a spontaneous depolarization R, also revealed by the M5 marker signal from EA) and the device continues to monitor the ventricular activity.

One skilled in the art will appreciate that the present invention can be practiced by other than the described embodiments, which are presented for purposes of illustration and not of limitation.

What is claimed is:

1. An implantable medical device comprising:
   a mechanical activity sensor configured to sense movements produced by contractions of a ventricular cavity and to output a mechanical activity signal representative of the contractions; and
   one or more circuits configured to:
      detect a plurality of spontaneous ventricular depolarizations based on electrical potentials representative of the spontaneous ventricular depolarizations;
      calculate an escape interval; and
      provide an antibradycardia ventricular pacing therapy in an absence of a detected spontaneous ventricular event after the escape interval;
   wherein the one or more circuits are configured to calculate the escape interval by:
      calculating a first escape interval based on successive detected spontaneous ventricular depolarizations;
      calculating a second escape interval based on the mechanical activity signal from the mechanical activity sensor; and
      selecting one of the first escape interval and the second escape interval, wherein the second escape interval is selected in response to a delivery of an antitachycardia atrial pacing therapy.

2. The device of claim 1, wherein the one or more circuits are configured to set the second escape interval to a predetermined minimum value when the calculated second escape interval is lower than the predetermined minimum value.

3. The device of claim 1, wherein the one or more circuits are configured to average a plurality of second escape intervals identified during successive cardiac cycles to calculate the second escape interval.

4. The device of claim 1, wherein:
   the mechanical activity sensor comprises an acceleration sensor configured to generate an endocardial acceleration signal; and
   the one or more circuits are configured to recognize and isolate in the endocardial acceleration signal a component corresponding to an endocardial acceleration peak associated with a ventricular contraction.

5. The device of claim 4, wherein the acceleration sensor comprises an endocardial sensor, an epicardial sensor, or a myocardium wall motion sensor.

6. The device of claim 1, wherein the mechanical activity sensor comprises at least one of a pressure sensor and an intracardiac impedance sensor.

7. The device of claim 1, wherein the implantable medical device is configured to perform at least one of cardiac stimulation, cardiac resynchronization, and cardiac defibrillation.

8. The device of claim 1, wherein the mechanical activity sensor is configured to detect in the mechanical activity signal a plurality of peak components associated with ventricular contractions, and wherein the one or more circuits are configured to calculate the second escape interval based on successive peak components detected by the mechanical activity sensor.

9. The device of claim 1, wherein the one or more circuits are configured to detect an occurrence of one or more spontaneous atrial events and one or more paced atrial events.

10. The device of claim 1, wherein the one or more circuits are configured with an atrial post-pacing refractory period, responsive to an atrial pacing event, during which ventricular electrical potential detection is blocked.

11. A method comprising:
   generating, using a mechanical activity sensor of an implantable medical device, a mechanical activity signal representative of contractions of a ventricular cavity;
   detecting, using one or more circuits of the implantable medical device, a plurality of spontaneous ventricular depolarizations based on electrical potentials representative of the spontaneous ventricular depolarizations;
   calculating, using the one or more circuits, an escape interval; and
   providing an antibradycardia ventricular pacing therapy in an absence of a detected spontaneous ventricular event after the escape interval;
   wherein calculating the escape interval comprises:
      calculating a first escape interval based on successive detected spontaneous ventricular depolarizations;

calculating a second escape interval based on the mechanical activity signal from the mechanical activity sensor; and selecting one of the first escape interval and the second escape interval, wherein the second escape interval is selected in response to a delivery of an antitachycardia atrial pacing therapy.

12. The method of claim 11, wherein calculating the second escape interval comprises setting the second escape interval to a predetermined minimum value when the calculated second escape interval is lower than the predetermined minimum value.

13. The method of claim 11, wherein calculating the second escape interval comprises averaging a plurality of second escape intervals identified during successive cardiac cycles.

14. The method of claim 11, wherein:
the mechanical activity sensor comprises an acceleration sensor configured to generate an endocardial acceleration signal; and
the method comprises recognizing and isolating in the endocardial acceleration signal a component corresponding to an endocardial acceleration peak associated with a ventricular contraction.

15. The method of claim 11, further comprising detecting, in the mechanical activity signal, a plurality of peak components associated with ventricular contractions, wherein the second escape interval is calculated based on successive peak components detected by the mechanical activity sensor.

16. A computer-readable storage medium having instructions stored thereon that, when executed by a processor of an implantable medical device, cause the implantable medical device to perform operations comprising:
generating, using a mechanical activity sensor of the implantable medical device, a mechanical activity signal representative of contractions of a ventricular cavity;
detecting a plurality of spontaneous ventricular depolarizations based on electrical potentials representative of the spontaneous ventricular depolarizations;
calculating an escape interval; and
providing an antibradycardia ventricular pacing therapy in an absence of a detected spontaneous ventricular event after the escape interval;
wherein calculating the escape interval comprises:
calculating a first escape interval based on successive detected spontaneous ventricular depolarizations;
calculating a second escape interval based on the mechanical activity signal from the mechanical activity sensor; and
selecting one of the first escape interval and the second escape interval, wherein the second escape interval is selected in response to a delivery of an antitachycardia atrial pacing therapy.

17. The computer-readable storage medium of claim 16, wherein calculating the second escape interval comprises setting the second escape interval to a predetermined minimum value when the calculated second escape interval is lower than the predetermined minimum value.

18. The computer-readable storage medium of claim 16, wherein calculating the second escape interval comprises averaging a plurality of second escape intervals identified during successive cardiac cycles.

19. The computer-readable storage medium of claim 16, wherein:
the mechanical activity sensor comprises an acceleration sensor configured to generate an endocardial acceleration signal; and
the operations comprise recognizing and isolating in the endocardial acceleration signal a component corresponding to an endocardial acceleration peak associated with a ventricular contraction.

20. The computer-readable storage medium of claim 16, wherein the operations further comprise detecting, in the mechanical activity signal, a plurality of peak components associated with ventricular contractions, wherein the second escape interval is calculated based on successive peak components detected by the mechanical activity sensor.

* * * * *